United States Patent [19]

Sasagawa et al.

[11] Patent Number: 4,967,269

[45] Date of Patent: Oct. 30, 1990

[54] ENDOSCOPE AUTOMATIC LIGHT CONTROL APPARATUS AND ENDOSCOPE APPARATUS MAKING USE OF THE SAME

[75] Inventors: Katsuyoshi Sasagawa; Masao Uehara; Akinobu Uchikubo; Katsuyuki Saito; Masahide Kanno; Masahiko Sasaki; Takehiro Nakagawa, all of Hachioji; Jun Hasegawa, Mino; Shinji Yamashita, Hachioji, all of Japan

[73] Assignee: Olympus Optical Co., Ltd., Tokyo, Japan

[21] Appl. No.: 343,718

[22] Filed: Apr. 27, 1989

[30] Foreign Application Priority Data

Jul. 28, 1988 [JP] Japan .................................. 63-188870

[51] Int. Cl.⁵ ........................ H04N 7/18; H04N 5/57
[52] U.S. Cl. ..................................... 358/98; 358/168; 358/169; 128/6
[58] Field of Search ......................... 358/98, 168, 169; 128/4, 6

[56] References Cited

U.S. PATENT DOCUMENTS

| | | | |
|---|---|---|---|
| 4,327,738 | 5/1982 | Green et al. ........................ | 358/98 |
| 4,475,539 | 10/1984 | Konomura ........................... | 358/98 |
| 4,532,918 | 8/1985 | Wheeler ............................... | 358/98 |
| 4,535,758 | 8/1985 | Longacre et al. ................... | 358/168 |
| 4,621,284 | 11/1986 | Nishioka et al. ..................... | 358/98 |
| 4,631,582 | 12/1986 | Nagasaki et al. .................... | 358/98 |
| 4,646,724 | 3/1987 | Sato et al. ............................ | 358/98 |
| 4,755,873 | 7/1988 | Kobayashi ........................... | 358/98 |
| 4,791,480 | 12/1988 | Muranaka ............................ | 358/98 |

Primary Examiner—John K. Peng

Attorney, Agent, or Firm—Armstrong, Nikaido, Marmelstein, Kubovcik & Murray

[57] ABSTRACT

An endoscope automatic light control apparatus comprises an automatic light control apparatus for controlling the quantity of light incident to an imaging apparatus for imaging an endoscopic image so as to maintain a signal from the imaging apparatus substantially at a constant level. An automatic gaim control apparatus inputs a signal from the imaging apparatus and controls its output level so as to maintain the signal substantially at a constant level. The automatic light control apparatus and the automatic gain control apparatus respectively having a plurality of brightness information generating apparatuses generating brightness information based on the signal from the imaging apparatus. The plurality of brightness information generating apparatuses are different from each other in a method of generating brightness information and one of the plurality of brightness information generating apparatuses able to be selected. A selecting apparatus selects the brightness generating apparatus of the same method as the automatic light control apparatus and as the automatic gain control apparatus. The automatic light control apparatus controls the quantity of light based on the brightness information and the automatic gain control apparatus controls its output level based on the brightness information. The endoscope apparatus further comprises an endoscope unit having an insert section with an observation window and an image forming optical system, an imaging apparatus, a signal processing apparatus and an illuminating system.

11 Claims, 11 Drawing Sheets

|   | 1 | 2 | 3 | 4 | 5 | 6 | 7 |
|---|---|---|---|---|---|---|---|
| 1 | G | Mg | G | Mg | G | Mg | G |
| 2 | Ye | Cy | Ye | Cy | Ye | Cy | Ye |
| 3 | G | Mg | G | Mg | G | Mg | G |
| 4 | Cy | Ye | Cy | Ye | Cy | Ye | Cy |
| 5 | G | Mg | G | Mg | G | Mg | G |
| ⋮ | Ye | Cy | Ye | Cy | Ye | Cy | Ye |
| ⋮ | G | Mg | G | Mg | G | Mg | G |

FIRST FIELD    SECOND FIELD

ENDOSCOPE AUTOMATIC LIGHT CONTROL APPARATUS AND ENDOSCOPE APPARATUS MAKING USE OF THE SAME

BACKGROUND OF THE INVENTION

1. Field of the Invention

The present invention relates to an endoscope automatic light control apparatus provided with an automatic light control means and an automatic gain control means, and relates to an endoscope apparatus making use of the same.

2. Related Art Statement

In recent years, endoscopes have been widely put into practical use which observe the internal organs in the body cavity by inserting an elongated insert section into the body cavity, and as occasion arises, are able to give various medical treatments by using instruments inserted into instrument channels.

Also, various electronic endoscopes have been proposed by using solid state imaging devices such as a charged coupled device(CCD) as an imaging means.

As an automatic light control means of the electronic endoscopes, there are electronic endoscopes wherein both an iris control means for controlling the quantity of illuminating light and an automatic gain control means for controlling its video signal output are used. For example, in the specification of Ser. No. 244,777, by means of establishing a switch for controlling the quantity of light of an operating panel, an electronic endoscope apparatus is proposed to expand the dynamic range and to realize a high-speed control with good response by changing the same quantity of the reference levels of an automatic light control means(ALC) and an automatic gain control means (AGC) to the same direction by using such an iris. Since endoscopes are used under a special condition that is a condition in the body cavity, special attention should be paid to a detecting circuit for detecting brightness information in the ALO and the AGC. For example, when a hollow portion such a the gullet is observed, it is desirable that a peak value detection for detecting a peak value of a signal as a controlling signal should be used. If an average value detection is used for detecting an average value of a signal as a controlling signal, a halation is apt to be generated and, according to circumstances, there is a case of being unable to control the quantity of light even if a switch for controlling the quantity of light is adjusted to the darkest. In contrast with this, in case forceps are used, because the ALC and the AGC respond to a part of forceps having a very high reflection factor unless an average detection is used, there is a defect that the part of observation becomes dark. For the reasons mentioned above, it is necessary for an electronic endoscope apparatus to change a peak value detecting circuit with an average detecting circuit as occasion arises.

In an automatic light control circuit by using both the ALC and the AGC, the ALC was able to change the peak value detection with the average value detection and the AGC was fixed on either the peak value detection or the average value detection so far.

According to such prior art, electronic endoscopes have the following defect when they are used. That is to say, in case the ALC uses the peak value detection and the AGC uses the average value detection, a detecting level of the AGC falls and the AGC operates in the direction of increasing the gain, because the ALC operates to adjust the brightness of a projection such as a polyp. As a result, the polyp becomes brighter than its adjustment. Also, because the gain of the AGC increases, a signal to noise ratio(S/N) becomes worse. In contrast with this, in case the ALC uses the average value detection and the AGC uses the peak value detection, there is a case where the peak value detecting circuit responds to a slight spot and it does not operate in the direction of increasing the gain and the observation scope becomes narrower, in spite of an opening of an iris's full width when the stomach walls are observed.

OBJECT AND SUMMARY OF THE INVENTION

An object of the present invention is to provide an endoscope automatic light control apparatus with an automatic light control means and an automatic gain control means is able to select an appropriate photometric system according to a using part and conditions of an endoscope and so on, and to provide an endoscope apparatus wherein the same is made use of.

An endoscope automatic light control apparatus of this invention comprises an automatic light control device for controlling the quantity of light incident to an imaging device for imaging an endoscopic image so as to maintain a signal from the imaging device substantially at a constant level. An automatic gain control device inputs the signal from the imaging device and controls its output level so as to maintain the signal substantially at a constant level. The automatic light control device and the automatic gain control device respectively have a plurality of brightness information generating devices which generate brightness information based on the signal from the imaging device. The plurality of brightness information generating device are different from each other in a method of generating brightness information. One of the plurality of brightness information generating device is able to be selected. The automatic light control device the automatic gain control device respectively have a selecting device for selecting the brightness information generating device of the same method as the automatic light control device and as the automatic gain control device in the plurality of brightness information generating devices. The automatic light control device controls the quantity of light based on the brightness information generated by the brightness information generating device selected by the selecting device. The automatic gain control device controls the output level based on the brightness information generated by the brightness information device selected by the selecting device. The endoscope apparatus, wherein the automatic light control apparatus is used, further comprises an endoscope unit having an elongated insert section provided at the tip part with an observation window and an image forming optical system for receiving light reflected from an object so as to form an image of the object. An imaging device images an image of the object formed thereon through the image forming optical system. A signal processing device processes a video signal derived from the imaging device and an illuminating device supplies illuminating light to a visual field of the image forming optical system.

The other features and advantages of the present invention will become apparent with the following explanation.

BRIEF DESCRIPTION OF THE DRAWINGS

FIGS. 1 to 11 relate to the first embodiment of the present invention.

FIGS. 12 to 17 relate to the second embodiment of the present invention.

DETAILED DESCRIPTION OF THE PREFERRED EMBODIMENTS

FIGS. 1 to 11 show the first embodiment of the present invention.

Figure 2:
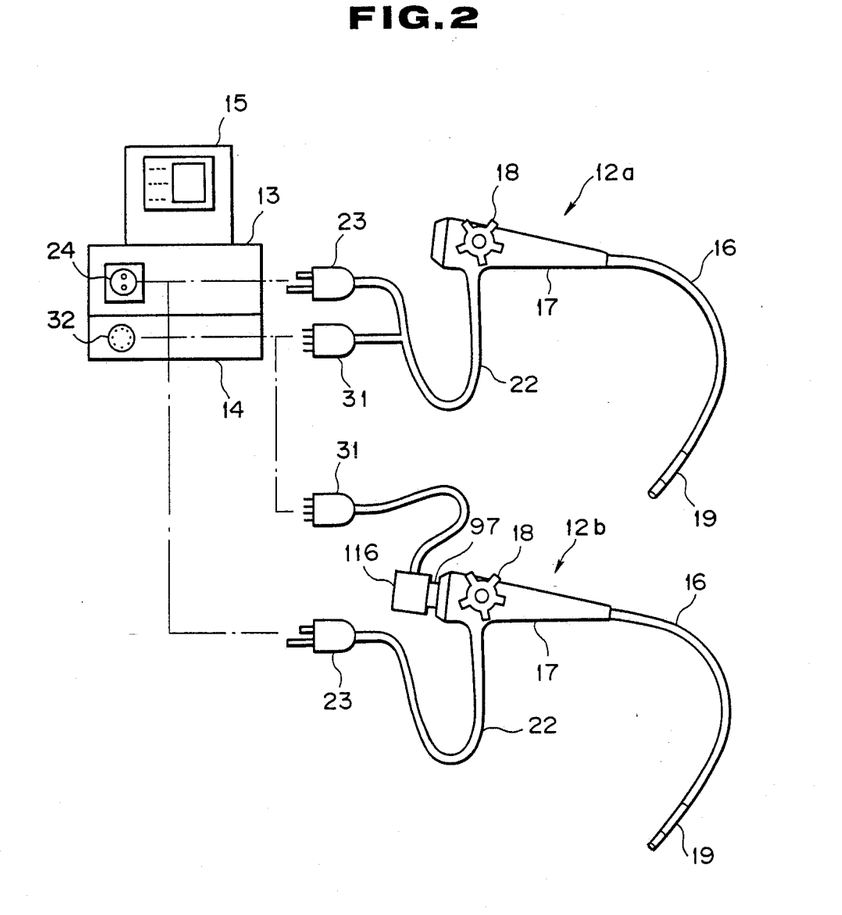
FIG. 2 is an illustration showing the whole of an electronic endoscope apparatus.

As shown in FIG. 2, an electronic endoscope apparatus ii has an endoscope 12a including an imaging means, a light source apparatus 13 providing illuminating light to the electronic endoscope 12a, a signal processing apparatus 14 processing a signal for the electronic endoscope 12a, and a color monitor 15 showing the color of a video signal output from the signal processing apparatus 14.

Also, a fiberscope 12b, and a television camera 116 which is attached to an eyepiece portion 97 of the fiberscope 12b, can be used in place of the electronic endoscope 12a.

Each of the above mentioned electronic endoscope 12a and the fiberscope 12b has an elongated insert section 16 so as to be able to be inserted into the body cavity. A thick manipulating portion 17 is formed in the rear end of the insert section 16. A curve portion 19 is formed beside the tip part of the insert section 16 so as to be able to bent up and down, and right and left by turning an angle knob 18 provided in the manipulating portion 17.

Figure 1:
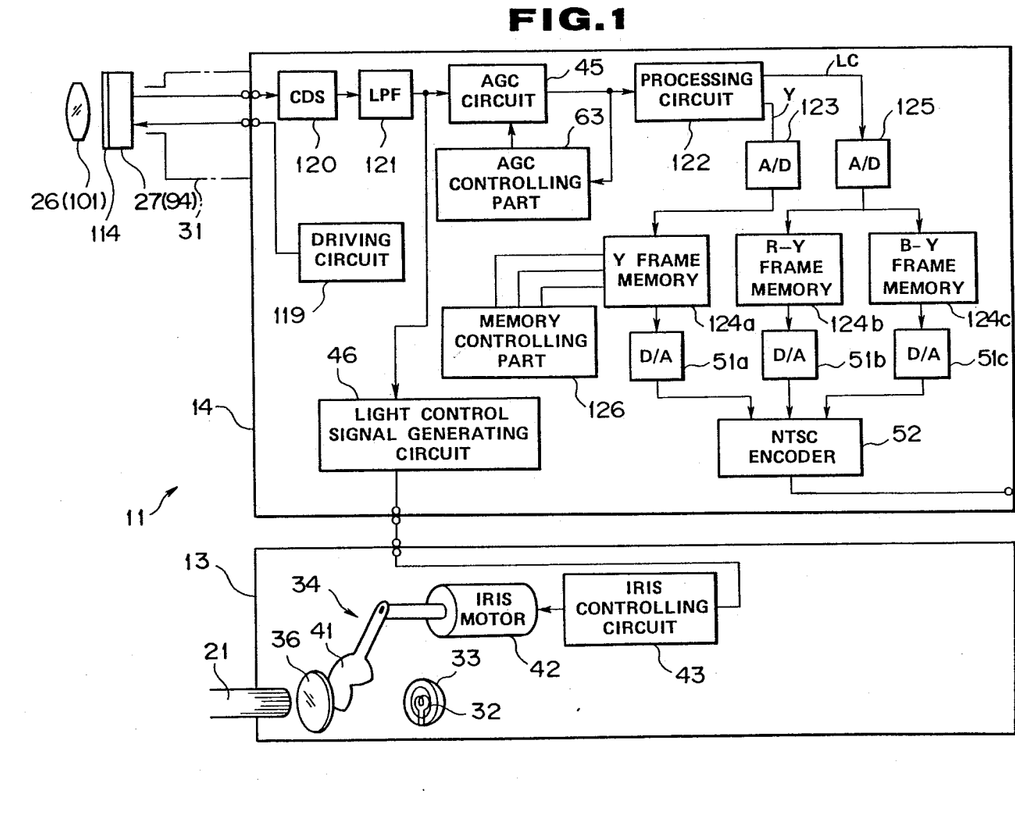
FIG. 1 is an illustration showing the formation of a signal processing apparatus and a light source apparatus in an electronic endoscope apparatus.

As shown in FIG. 1, the light source apparatus 13 has a lamp 32 which radiates white light, a concave lens 33 which emanates the white light of the lamp 32 in a parallel light beam, an Iris apparatus 34 which is brought in the way of the parallel light beam so as to be able to change the quantity of light passed through, and a condenser lens 36 wherein the light having passed through the iris apparatus 34 is converged on an incident end surface of a light guide 21 mentioned in the following.

The above mentioned iris apparatus 34 comprises an iris plume 41 forming a slit and an iris motor 42 wherein the base end of the iris plume 41 is fitted to and the iris plume is rotated in the vertical direction of an optical axis so as to reduce the quantity of the light passed through. The rotation of the iris motor 42 is controlled by a driving signal from an iris controlling circuit 4S so as to be able to control the quantity of light by the quantity of the rotation(rotary angle).

Figure 3:
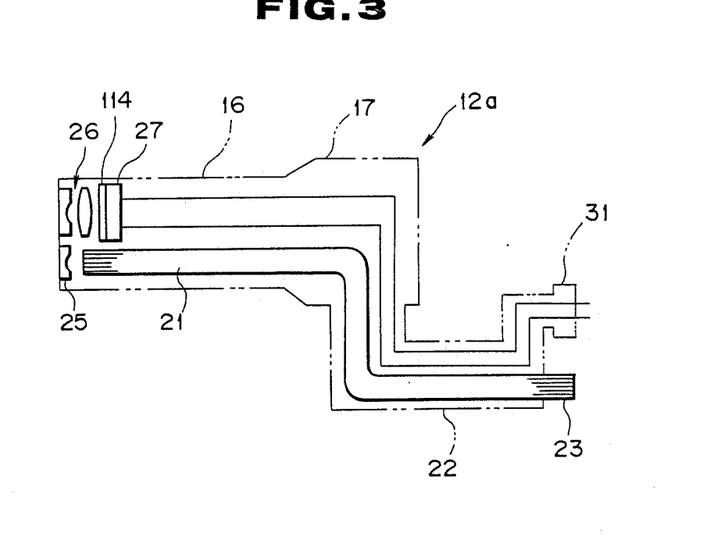
FIG. 3 is an illustration showing the formation of an electronic endoscope.
Figure 4:
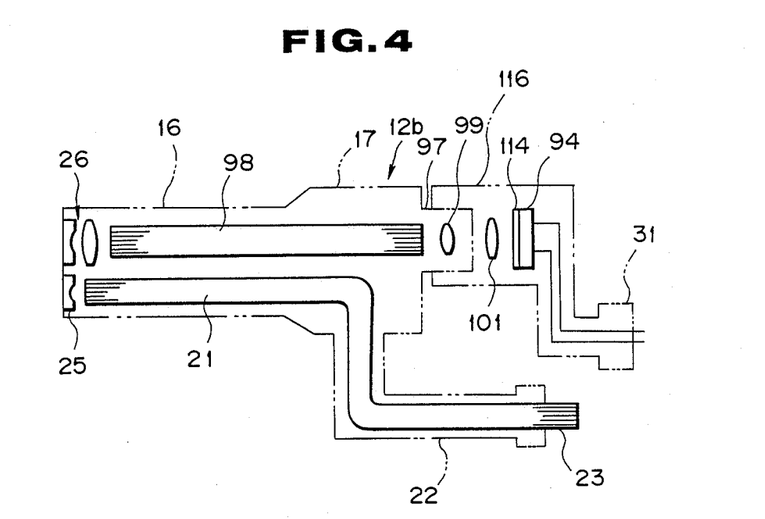
FIG. 4 is an illustration showing the formation of a fiberscope and a television camera.

Within the above mentioned insert section 16 of the electronic endoscope 12a and the fiberscope 12b, the light guide 21 is inserted as shown in FIGS. 3 and 4, and is further inserted in a light guide cable 22 extended from the manipulating portion 17, and a connector 23 for the light source is fitted to the end of the light guide cable 22 so as to be able to connect to a connector receiver 24 of the light source apparatus 13. Illuminating light is provided on the incident end surface of the light guide 21 and is transmitted by the light guide 21. The illuminating light is emanated from the emanating end surface of the light guide 21 and is further expanded by way of a light distribution lens 25. Accordingly, the side of an object is illuminated.

In he endoscope 12a as shown in FIG. 3, the object is illuminated by the illuminating light by way of the above mentioned light distribution lens 25 and is formed an image on a CCD 27 as a solid state imaging device disposed on the focal plane thereof by an objective lens 26 fitted to the tip part of the insert section 16. The image of the object is photoelectrically converted in the CCD 27. A color mosaic filter 114 is attached on the front surface of the CCD 27. Therefore, a picture signal is read from the CCD 27 by applying a CCD driving signal output from a CCD driving circuit 119 within the signal processing apparatus 14 as shown in FIG. 1. The CCD driving signal and the picture signal are transmitted by a signal cable. A signal connector 31 is provided at the end of the signal cable so as to be able to connect to a connector receiver 32 provided in the signal processing apparatus 14.

On the other hand, in case of the fiberscope 12b, an object forms an image at the tip of an image guide 98 disposed on a focal plane of the objective lens 26 attached to the tip part of the insert section 16. The image guide 98 is inserted through the insert section 16 and the end surface of the image guide 98 is opposed to an eyepiece lens 99 in the eyepiece portion 97. The television camera 116 attached to the eyepiece portion 97 has an image forming lens 101 and a CCD 94 disposed on the focal plane of the image forming lens 101. A color mosaic filter 114 is attached on the front surface of the CCD 94. The CCD 94 is connected to the signal connector 31 provided in the end thereof by the signal cable the same as CCD 27. The signal connector 31 can be connected to the connector receiver 32 in the signal processing apparatus 14. Like the CCD 27, the picture signal is read by applying the CCD driving signal output from a CCD driving circuit 119.

Thus, the reflected light on an illuminated object forms an optical image on an focal plane thereof by the objective lens 26. In case of the electronic endoscope 12a, the CCD; to which a color mosaic filter 114 is attached, is disposed on the focal plane and the color of the image of the object is separated in each pixel of the color mosaic filter 114. On the other hand, in case of the fiberscope 12b, an incident end of the image guide 98 is disposed on the focal plane and the image of the object is formed as an image on the CCD 94 to which the color mosaic filter 114 is attached by way of the eyepiece lens 99 and the image forming lens 101 after the image of the object is transmitted by the image guide 98.

Figure 5:
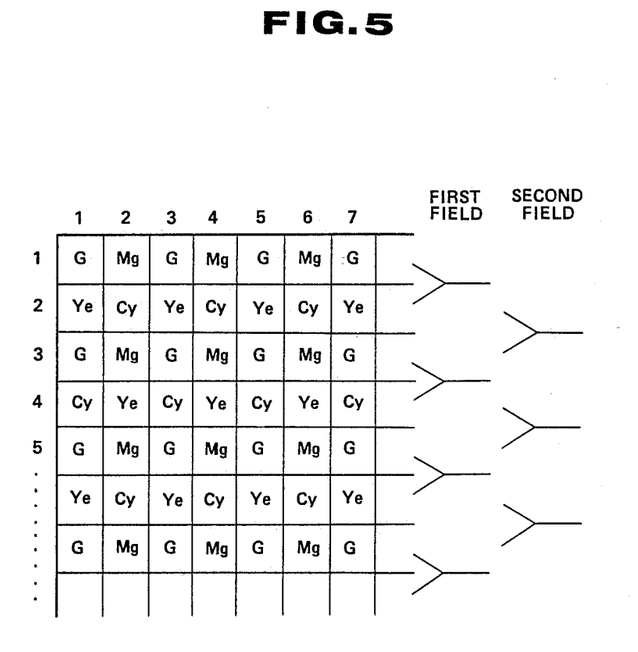
FIG. 5 is an illustration showing a color mosaic filter.

The color mosaic filter 114 attached to the front surface of the above mentioned CCD 27 or CCD 94 is a complementary color mosaic filter, such as shown in FIG. 5.

The CCD 27 or 94 attached by the complementary color mosaic filter 114 is, for example, a CCD of an interline transfer type in which a light receiving part(an accumulation part that accmulates light as an electric charge which is photoelectrically converted) and a transmitting part that transmits the accumulated electric charge, are reciprocally disposed.

Accordingly, the CCD 27 or 29 is read by the driving signal output from the driving circuit 119 as shown in FIG. 1. In this case as shown in FIG. 5, the CCD 27 or 94 conducts an interlace scanning system in which signals of two lines that are an odd line and an even line adjoining up and down, such as the first line and the second line, the third line and the fourth line and so on, are added and output in the first field, and in which signals of two lines that are an odd line and an even line adjoining up and down, such as the second line and the third line, the fourth Line and the fifth line and so on, are added and output in the second field.

Combinations of a total of four pixels which are two pixels adjoining up and down and two pixels adjoining right and left are all of the combinations of Ye, Mg, Oy and G. If these are added, 2R+3G+2B is obtained and is considered a luminance signal.

Two lines adjoining up and down are added in the CCD 27 or 94, and two lines adjoining right and left are added by intergrating them through a low-pass filter(LPF) 121 after a clock element is removed in a correlative double sampling(CDS) circuit 120 in the signal processing apparatus 14.

A signal passed through the LPF 121 is input in an AGC circuit 45 and a light control signal generating circuit 46. An output signal from the AGC circuit 45 is input in a processing circuit 122 and a AGC control part 63 which controls the gain of the AGC circuit 45. After such a color separation and γ revision are processed by the above mentioned processing circuit 122, a luminance signal Y and a line sequential color-difference signal LC are output.

The above mentioned luminance signal Y is converted into the digital quantity by an A/D converter 123 and housed in a Y frame memory 124a. Since color-difference signals R-Y and B-Y of the color-difference signal LC are sequentially(reciprocally) output in every line, the signal of R-Y line is housed in a R-Y frame memory 124b and the signal of B-Y line is housed in a B-Y frame memory 124c after the color-difference signal LC is converted into the digital quantity in the A/D converter.

The above mentioned Y frame memory 124a is sequentially read in every line. On the other hand, since there are signals for R-Y and B-Y in every two lines, they coincide with the luminance signal Y by reading the same signal in every two lines Writing and reading in the above mentioned frame memory 124a, 124b and 124c are controlled by a memory control part 126.

After a signal read from the above mentioned frame memory 124a, 124b and 124c is converted into an analog signal in a D/A converter 51a, 51b and 51c, the signal is input in a NTSC encoder 52, converted into a NTSC composite video signal, and output from an output end into a color monitor.

The above mentioned light control signal generating circuit 46 inputs a light control signal, in which a video signal is established in an appropriate level corresponding to an input video signal level, into the iris control circuit 43. The iris control circuit 43 controls the quantity of light through the iris plume 41 by driving the iris motor 42 and controls the quantity of an incident light to the light guide 21.

That is to say, the quantity of illuminating light is controlled according to the level of video signal which is input into the light control signal generating circuit 46 through the LPF 121.

In this manner, in case the endoscope apparatus is used in different circumstances, for example, used from a short distance to a relatively long distance, it can automatically establish the appropriate intensity of illumination by controlling the quantity of illuminating light so as to be able to obtain an image which is easily diagnosed or examined.

Figure 6:
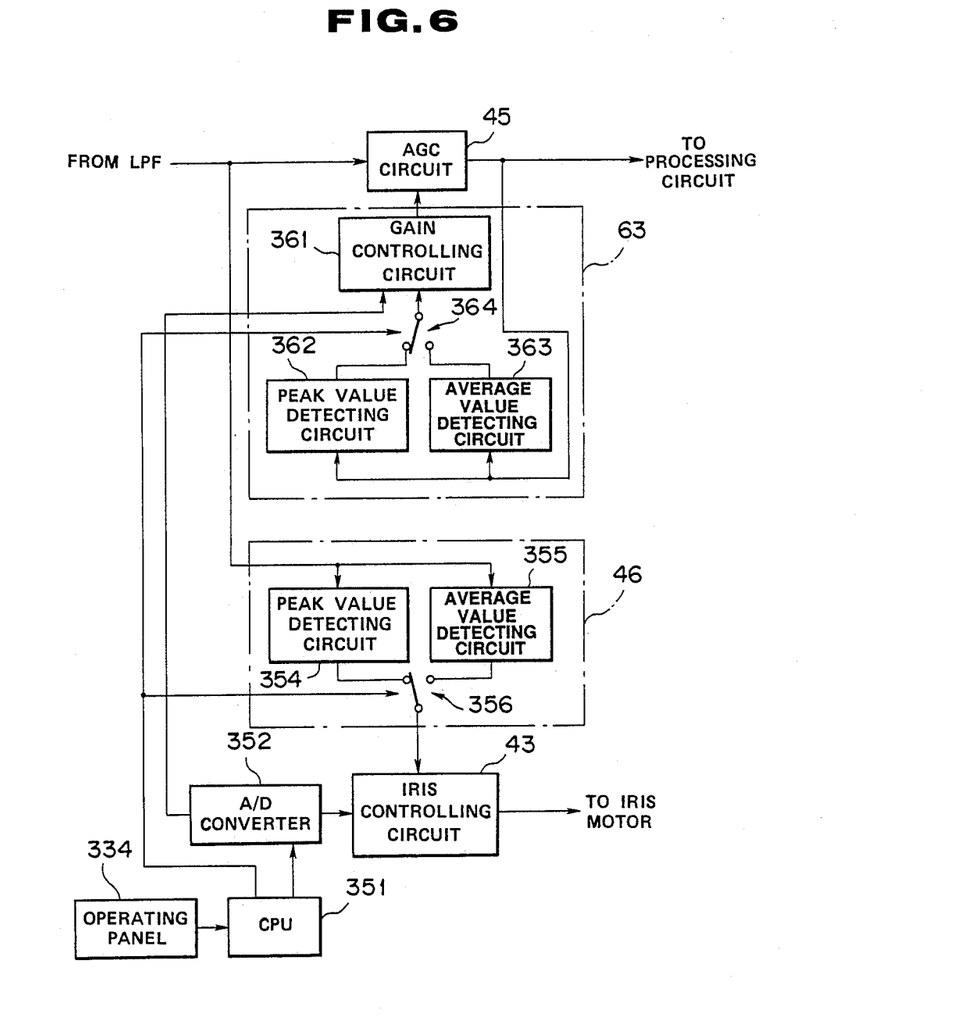
FIG. 6 is a block diagram showing the formation of an automatic light control means.

The automatic light control means in the embodiment is formed as shown in FIG. 6.

The light source apparatus 13 is provided with a CPU 351 wherein a switching signal, is input after being selected by a brightness establishing value from a brightness establishing means provided on an operating panel 334 and a detecting method switching means. The brightness establishing value taken in the CPU 351 is converted into an analog signal by an A/D converter 352 and transmitted to the iris control circuit 43 which controls the iris motor 42.

Also, as a plurality of brightness information generating means, the light control signal generating circuit 46 is provided with a peak value detecting circuit 354 which detects a peak value of a video signal as a control signal and an average value detecting circuit 355 which detects an average value of a video signal as a control signal. A video signal from the LPF 121 is input into the peak value detecting circuit 354 and the average value detecting circuit 355. Each output end of the peak value detecting circuit 354 and the average value detecting circuit 355 is connected to each input end of a switch 356 with two inputs and one output. The output end of the switch 356 is connected to the iris control circuit 43. The switch 356 is controlled by the CPU 351 and selects either the output of the peak value detecting circuit 354 or of the average value detecting circuit 355 according to the establishment of the operating panel 334, and then either the peak or average value to the iris control circuit 43.

Figure 7:
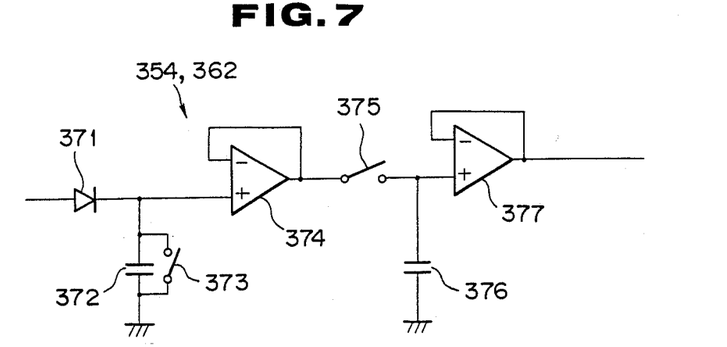
FIG. 7 is a circuit diagram showing a peak value detecting circuit.

The peak value detecting circuit 354 is formed as shown in FIG. 7. That is to say, the input end of the peak value detecting circuit 354 is connected to the positive pole of a diode 371. The negative pole of the diode 371 is connected to a non-inverting input end of an operational amplifier 374 and grounded by way of a hold condenser 372. Both ends of the hold condenser 372 are connected by way of a switch 373. Also, the output end of the operational amplifier 374 is connected to a non-inverting input end of an operational amplifier 377 by way of a switch 375 and grounded by way of a hold condenser 376. Then, the output of the operational amplifier 377 becomes the output of the peak value detecting circuit 354.

Figure 9:
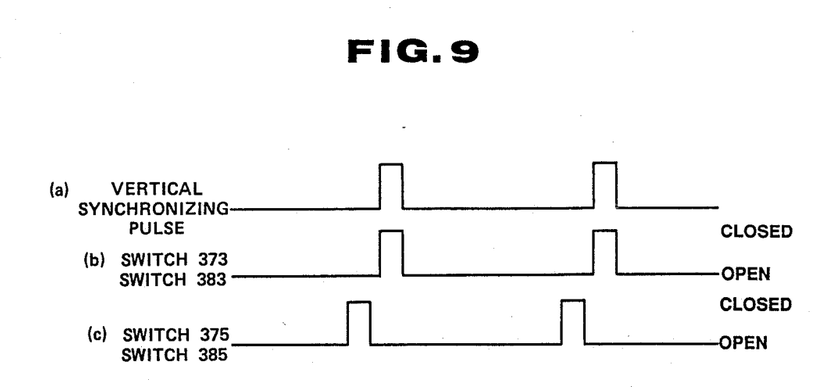
FIG. 9 is a timing chart showing the timing of an operation of a switch in a peak value detecting circuit and an average value detecting circuit.

The operation of the peak value detecting circuit 354 is illustrated as shown in FIG. 9. In the period of each field of vertical synchronizing pulse VD as shown in FIG. 9(a), the switch 373 is closed and the electric charge of the hold condenser 372 is emptied, and then the maximum level (peak value) of a video signal in one field period is held by the diode 371 and the condenser 372, and buffered by the operational amplifier 374. The switch 375 is closed just before the vertical synchronizing VD as shown in FIG. 9(c), and a peak value of a video signal is charged in the hold condenser 376 and held for one field period. Then, the peak value is output by way of the operational amplifier 377. Thus, the peak value of a video signal from the signal processing circuit 336 can be detected in every field.

Figure 8:
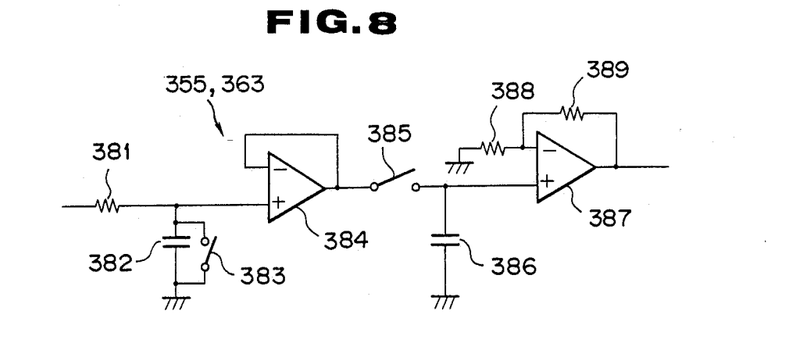
FIG. 8 is a circuit diagram showing an average value detecting circuit.

On the other hand, the average value detecting circuit 355 is formed as shown in FIG. 8.

That is to say, the input end of the average value detecting circuit 355 is connected to a non-inverting end of an operational amplifier 384 by way of a resistance 381 and grounded by way of a hold condenser 382. Both ends of the hold condenser 382 are connected by way of a switch 383. Also, the output end of the operational amplifier 384 is connected to a non-inverting end of an operational amplifier 387 by way of a switch 885 and grounded by way of a hold condenser 386. The operational amplifier 387 is negatively fed back by way of a resistance 389. Also, the non-inverting end of the operational amplifier 387 is grounded by way of a resistance 388. Then, the output of the operational amplifier 387 becomes the output of the average value detecting circuit 355.

The operation of the average value detecting circuit 355 is illustrated as shown in FIG. 9. As in the peak value detecting circuit 354, the switches 383 and 385 are open and closed by the timing shown in FIGS. 9(b) and (c). Then, a video signal of one field is integrated by the resistance 381 and the condenser 382. The integral value is amplified by an amplifier which consists of the operational amplifier 387 and the resistances 388 and 389. This is amplified because an average value detection which becomes a lower level as compared with a peak value detection is revised.

Also, said iris control circuit 43 compares the brightness establishing value and an output level of a detecting circuit, and controls the iris motor 42 so as to maintain the output of the detecting circuit at a constant level at all times. That is to say, if the average value detecting circuit 855 is selected, it operates so as to maintain an average level of an image(brightness) at a constant level, and if the peak value detecting circuit 354 is selected, it operates so as to maintain a peak of an image(the brightest part) at a constant level. Also, in case the brightness establishing value varies, a video signal which is maintained at a constant level varies in accordance with the brightness establishing value.

On the other hand, in the signal processing apparatus 14, the output of the LPF 121 is input into the AGC circuit 45 and the degree of amplification is controlled by a gain control circuit 361 provided in an AGC controlling part 63. The AGC controlling part 63 has a peak value detecting circuit 362 and an average value detecting circuit 363 as a plurality of brightness information generating means, and a video signal from the AGC circuit 45 is input into the peak value detecting circuit 362 and the average value detecting circuit 363. Further, the peak value detecting circuit 362 and the average value detecting circuit 363 have the same formation as the peak value detecting circuit 354 and the average value detecting circuit 355 of the light control signal generating circuit 46. Each output end of the peak value detecting circuit 362 and the average value detecting circuit 363 is connected to each input end of a switch 364 with two inputs and one output. The output end of the switch 364 is connected to the gain control circuit 361. The switch 364 is controlled its switching by the CPU 351, and selects either the output of the peak value detecting circuit or of the average value detecting circuit 363 and outputs to the gain control circuit 361. Also, the said switch 364 is geared to the switch 356 of the light control signal generating circuit 46 and selects a detecting circuit of the same method of the detecting circuit used in an iris control. In the gain control circuit 361, the brightness establishing value is input from the A/D converter 352, and the gain control circuit 361 compares a detecting level of either the peak value detecting circuit 362 or the average value detecting circuit 363 which is selected and a brightness establishing level, and controls the AGC circuit 45 in order to maintain an output of a detecting circuit at a constant level at all times. That is to say, if the average detecting circuit 363 is selected, the gain control circuit 361 operates to maintain an average level(brightness) of an image at a constant level, and if the peak value detecting circuit is selected, it operates to maintain a peak of an image(the brightest part) at a constant level. Also, in case the brightness establishing value varies, a video signal which is maintained at a constant level varies in accordance with the brightness establishing value.

In the embodiment, the time constant of an automatic gain control means (abbreviated as AGC in the following) using the AGC circuit 45 in the signal processing apparatus 14 is later(larger) than the time constant of an automatic light control means(abbreviated as ALC in the following) using the iris apparatus 34 in the light source apparatus 13. Also, the scope of the gain of the AGC is adjusted only in the direction of increasing a gain from 0 to 12 dB. While the ALC is operating, that is to say, until an iris fully opens, the gain of the AGC is adjusted to 0 dB. In other words, the AGC first operates after adjusting the limit of the ALC. In case the degree of electric amplification is adjusted to be higher than the standard, noises increases. Thus, this is conducted so as not to deteriorate the S/N.

Figure 10:
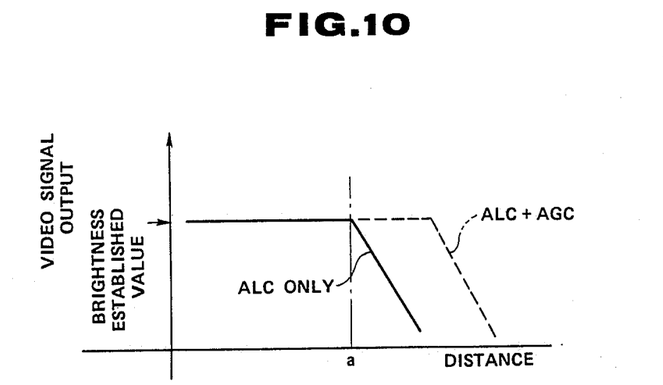
FIG. 10 is an illustration diagram showing the relationship between the distance from the tip part of an endoscope to an object, and an imaging signal output.
Figure 11:
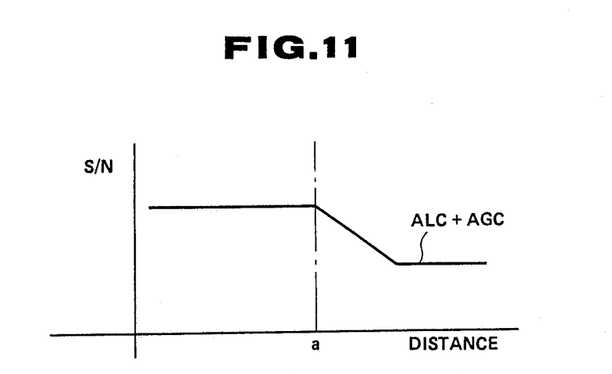
FIG. 11 is an illustration showing the relationship between the distance from the tip part of an endoscope to an object, and a S/N.

In FIG. 10, the relation between the distance from the tip of an endoscope to an object and an output of a video signal is shown. In FIG. 10, a part of a solid line indicates only an operation of the ALC, and a part of a broken line indicates an operation of a combination of the ALC and the AGC. According to this embodiment, the brightness can be surely maintained at a constant level to the distance "a" by the operation of the ALC and without using a detecting method and a brightness establishing level. As shown in FIG. 11, the operation of the AGC having relation to a change for the worse of the S/N first operates when an iris fully opens. Also, as shown in FIG. 1, the AGC is provided in a rear stage of the ALC.

Thus, in the embodiment, since the ALC and the AGC are provided, it becomes possible that an automatic light control function has a wide dynamic range and a high-speed control with good response. Also, because the peak value detecting circuit and the average value detecting circuit are provided in each of the ALC and the AGC and each detecting circuit of the same detecting method can be simultaneously switched, an appropriate photometric system can be selected according to a using part of an endoscope, conditions and so on.

Furthermore, since the detecting methods of the ALC and the AGC are simultaneously switched to the same methods, the gain of the AGC is not unnecessarily increased with a change for the worse of the S/N in an electronic endoscope which is somewhat insufficient of the quantity of light in the light source. Also, the gain of the AGC has been certainly increased when the quantity of light is not sufficient.

Also, in this embodiment, since the AGC operates after an iris fully opens, a good S/N is obtained only by the operation of the ALC and the brightness does not suddenly vary at the point of the full opening of the iris even if either the detecting method of the peak value detecting or of the average value detecting is used.

FIGS. 12 to 17 show the second embodiment of the present invention. This embodiment is an example of a frame sequential system which separates the color of an image of an object in a time series.

Figure 12:
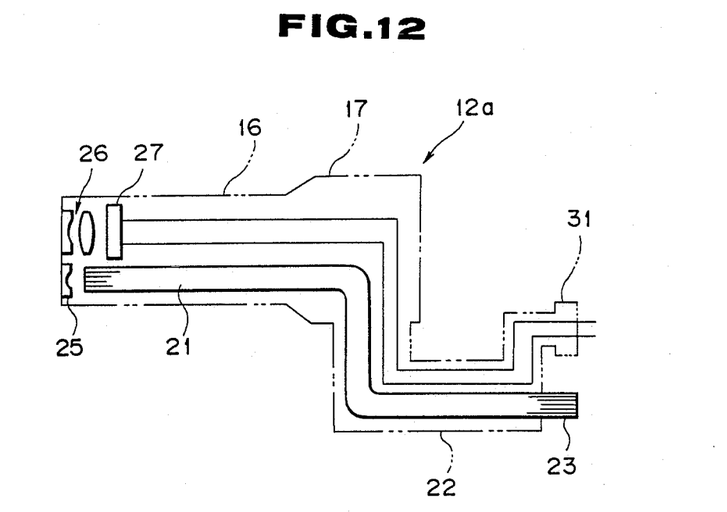
FIG. 12 is an illustration showing the formation of an electronic endoscope.
Figure 13:
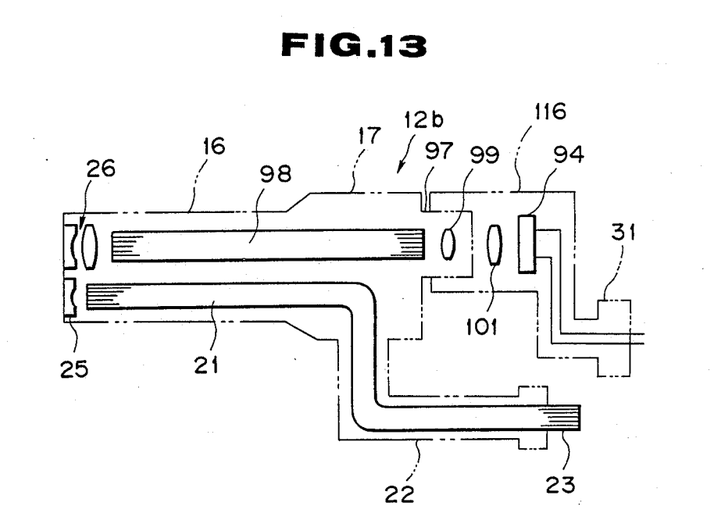
FIG. 13 is an illustration showing the formation of a fiberscope and a television camera.

As shown in FIGS. 12 and 13, the formation of the electronic endoscope 12a, the fiberscope 12b and the television camera 116 is substantially the same as the first embodiment; however, the color mosaic filter 114 is not provided on the front surface of the CCD 27 and 94.

Figure 14:
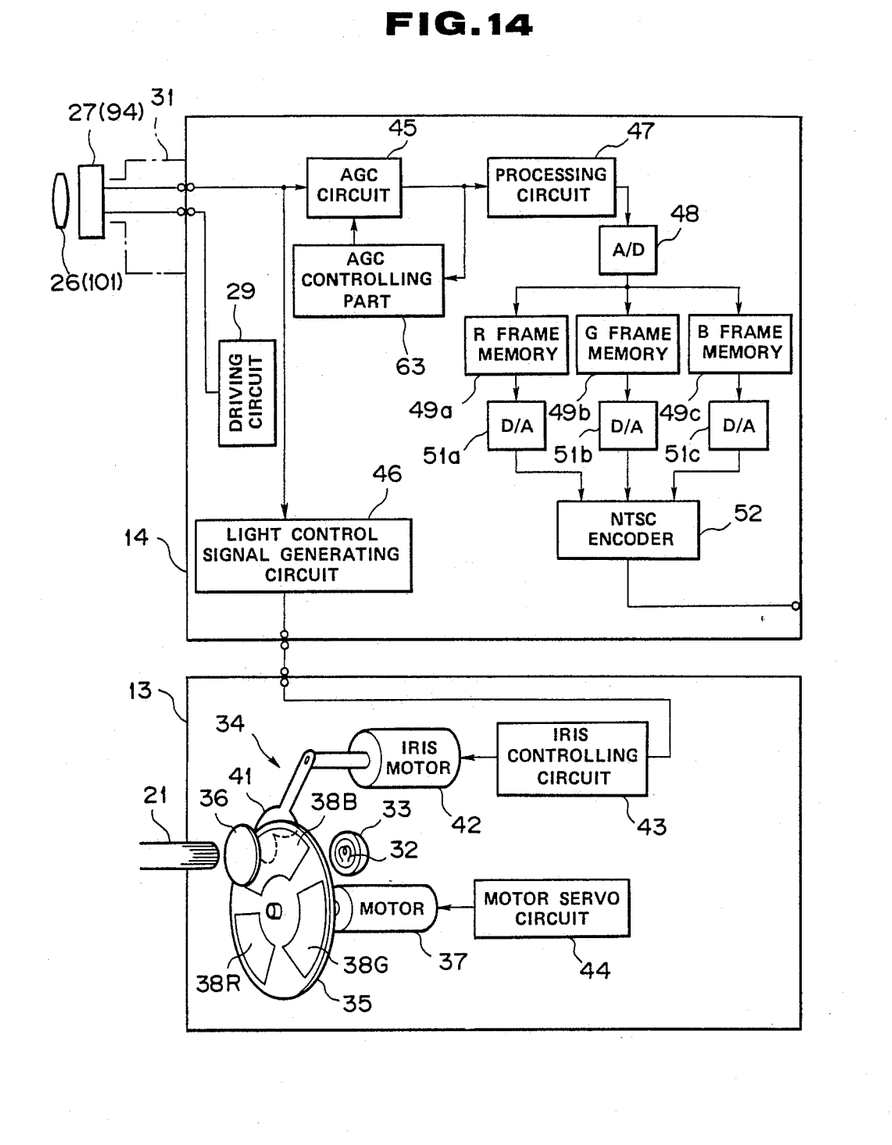
FIG. 14 is an illustration showing the formation of a signal processing apparatus and a light source apparatus in an electronic endoscope apparatus.

As shown in FIG. 14, the light source apparatus 13 has the lamp 32 which radiates white light, the concave lens 33 which emanates the white light of the lamp 32 in a parallel light beam, an iris apparatus 34 Which is brought in the way of the parallel light beam so as to be able to change the quantity of the light passed through, a rotary color filter 35 wherein the illuminating light is stopped down by the iris apparatus 34 and is separated into the component light of three primary colors of red, green and blue, and the condenser lens 36 wherein the light component of three primary colors having passed through the rotary color filter 35 is converged on an incident end surface of the light guide.

The above mentioned rotary color filter 35 has three fan shaped openings on a rotary disc frame which is rotated by a motor 37. Color transmitting filters 38R, 38G and 38B, which transmit the light of each wavelength of red, green and blue respectively, are fitted on the openings. Parts between the color transmitting filters 38R, 38G and 38B are formed by a shading member. Thus, each color of the transmitting filters 38R. 38G and 38B is sequentially brought into the optical path, and an object is frame sequentially illuminated by the light colors red, green and blue, and then imaged by the CCD 27 and 94 under the illumination of each color light. Thus, in the shading period by the shading member, the CCD driving signal is applied and is photoelectrically converted, respectively. Then, a video signal accumulated as an electric charge is read and a color imaging of the frame sequential type can be conducted by processing the video signal which is imaged under the illumination of each light of these colors.

Further, the motor 37 which rotates the rotary color filter 35 is controlled by a motor servo circuit 44 so as to maintain its rotary speed as a constant level.

The video signal is read from the CCD 27 and 94 by applying the CCD driving signal and inputted into the AGC circuit 45 after carriers are removed in a preprocessing circuit which is not illustrated, and the video signal is input into the light control signal generating circuit 46 which generates a light control signal. The output signal of the above mentioned AGC circuit 45 is input into a processing circuit 47 and dealt with a process such as white balance and Knee. The output of this processing circuit 47 is input into a A/D converter 48 and converted into a digital signal. This digital signal is sequentially retained as picture data per one picture (frame) in a R frame memory 49a, G frame memory 49b and B frame memory 49c which are provided corresponding to each color field. For example, a video signal imaged under red illuminating light is stored in the R frame memory 49a. Thus, the picture data stored in the R frame memory 49a, the G frame memory 40b and the B frame memory 49c are simultameously read, and converted into an analog color signal by way of D/A converters 51a, 51b and 51c, respectively. Then, the picture data are converted into a composite video signal of the NTSC method in the NTSC encoder 52 and output into the monitor side.

Further, the light control generating circuit 46 outputs a light control signal into an iris controlling circuit 43 in order that the light control signal is maintained at an appropriate level of a video signal corresponding to a signal input, and controls the quantity of stopping down. By this light control signal, in case use conditions are different, for example, from a short distance to relatively a long distance, the quantity of illuminating light is controlled and automatically adjusted to the appropriate intensity of illumination so as to be able to obtain an image which is easily diagnosed or examined.

Figure 15:
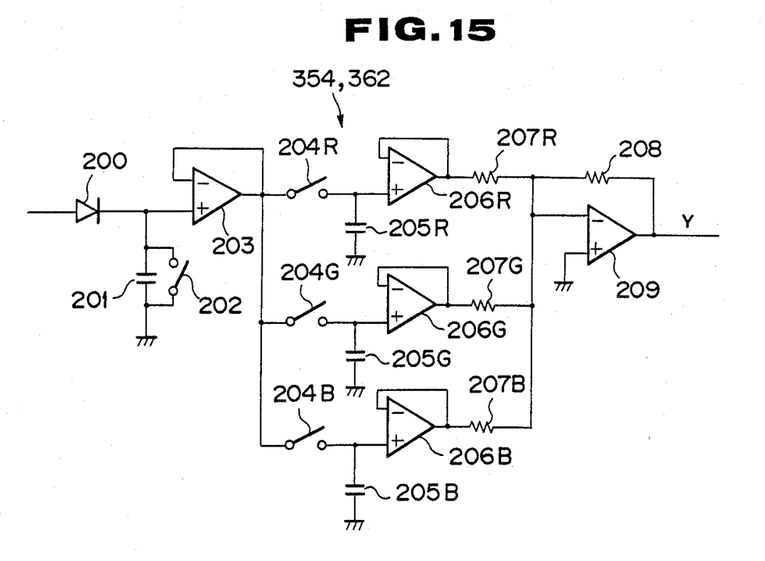
FIG. 15 is a circuit diagram showing a peak value detecting circuit.

In this embodiment, the light control generating circuit 46 and the AGC controlling part 63 are formed as shown in FIG. 6. However, in this embodiment, the peak value detecting circuits 354 and 362 are formed as shown in FIG. 15 and the average value detecting circuits 355 and 363 are formed as shown in FIG. 16.

That is to say, the input ends of the peak value detecting circuits 354 and 362 are connected to the positive pole of a diode 200. The negative pole of the diode 200 is connected to a non-inverting input end of an operational amplifier 203 and grounded by way of a condenser 201. Both ends of the condenser 201 are connected by way of a switch 202. Also, the output end of the operational amplifier 203 is connected to non-inverting input end of operational amplifiers 206R, 206G and 206B, respectively, by way of switches 204R, 204G and 204B, and grounded by way of hold condensers 205R, 205G and 205B, respectively. The output ends of the operational amplifier 206R, 206G and 206B are connected to an inverting input end of an operational amplifier 209 by way of resistances 207R, 207G and 207B, respectively. The non-inverting input end of the operational amplifier 209 is grounded and its output end is connected to its inverting input end by way of a resistence 208. The output of the operational amplifier 209 becomes the output of the peak value detecting circuits 354 and 362.

Figure 17:
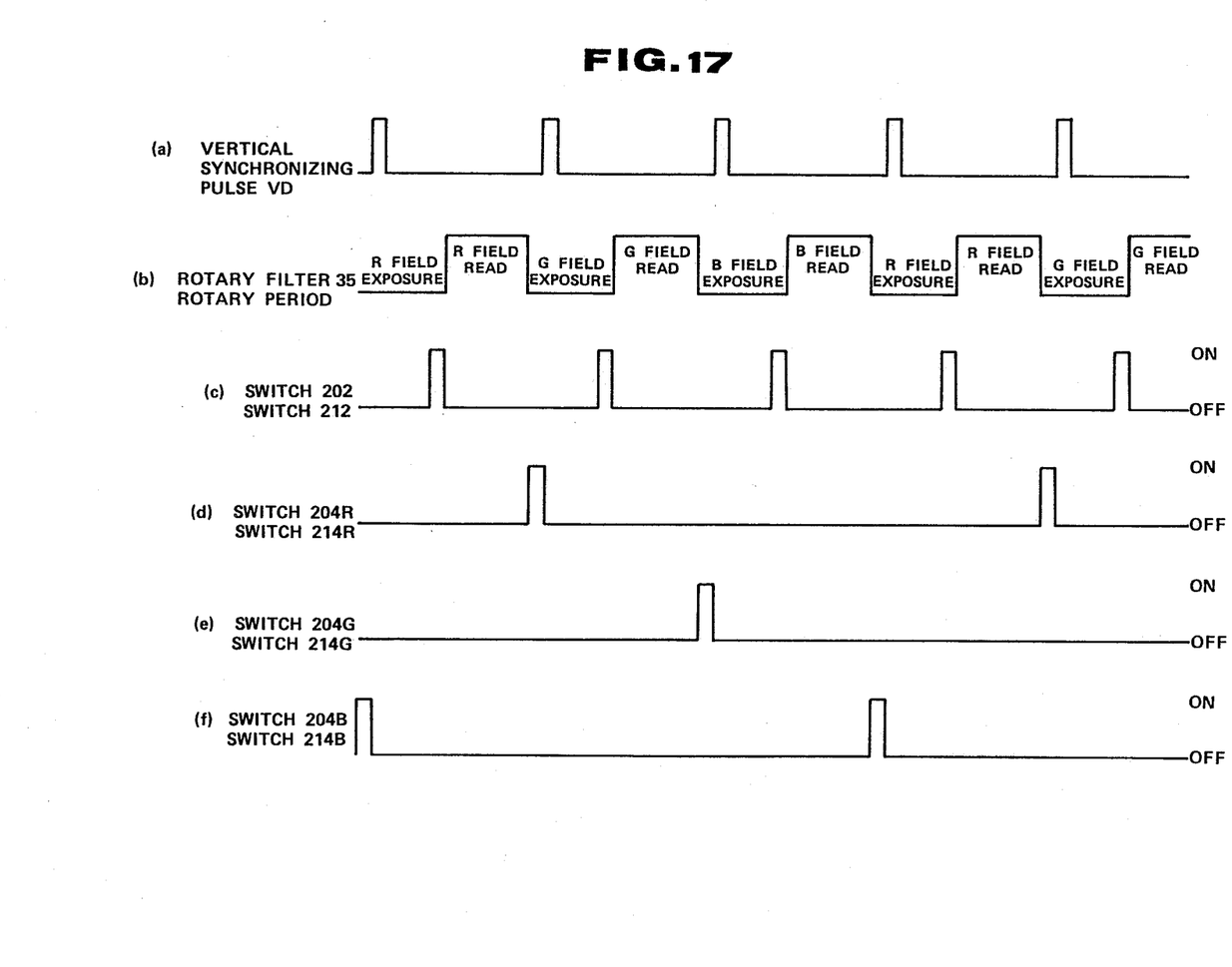
FIG. 17 is a timing chart showing a timing of an operation of a switch in a peak value detecting circuit and an average value detecting circuit.

The operations of the peak value detecting circuits 354 and 362 are illustrated as shown in FIG. 17. In this embodiment, the rotary filter 35 is rotating at 20 Hz as shown in FIGS. 17(a) and (b) By rotating the rotary filter 35 at 20 Hz, a color field of 60 fields per one second is generated. Since this is the same field frequency of the NTSO method, it is possible to expose in the first half of one field period and read in the second half of one field period. The switch 202 is a reset switch which is turned on just before a reading period of each color field as shown in FIG. 17(c), and the electric charge in the condenser 201 is swept up. Afterward, the maximum level of a video signal in one field period is held by the diode 200 and the condenser 201, and buffered by the operational amplifier 203. The switches 204R, 204G and 204B are turned on just after completing the reading period of each corresponding color field as shown in FIGS. 17(d), (e) and (f), respectively. A peak value of a video signal is charged in the condensers 205R, 205G and 205B and held for three field periods until the next corresponding color field. The peak value of each color sampled and held is added by the resistances 207R, 207G and 207B, the resistence 208 and the operational amplifier 209 (the polarity is inverted). The ratio of the resistances 207R to 207G to 207B is established in order that, for example, the ratio of R to G to B is in accord with the Y signal of the NTSC signal In case a white object is imaged, the adding ratio of Y to R, G and B is $Y=0.3R+0.6G+0.1B$, if an input into the diode 200 has the ratio of R:G:B=1:1:1. Therefore, the resistances 207R, 207G and 207B are established by the ratio of 207R:207G 207B=1/0.3:1/0.6:1/0.1=2:1:6. Accordingly, the Y signal, which coincides with the ALC and the AGC from the color frame sequential signal and is detected by its peak value, can be obtained.

Figure 16:
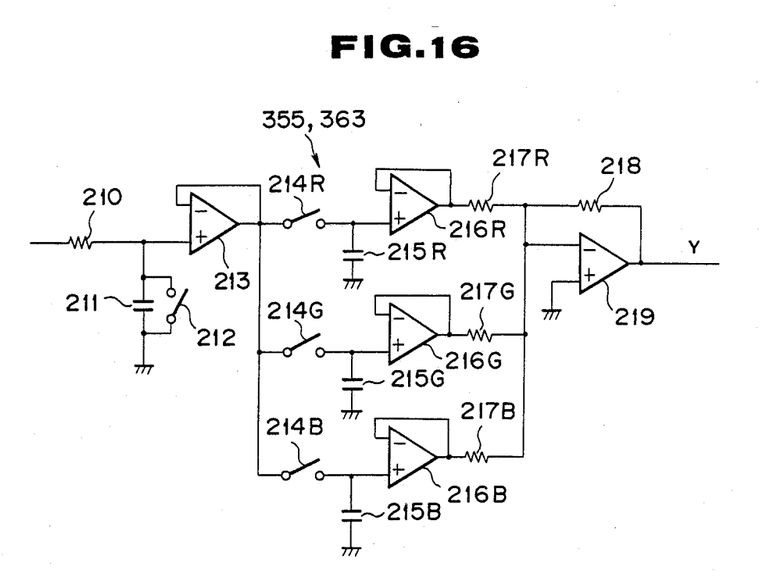
FIG. 16 is a circuit diagram showing an average value detecting circuit.

On the other hand, as shown in FIG. 16, the input ends of the average value detecting circuits 355 and 363 are connected to a non-inverting input end of an operational amplifier 213 by way of a resistance 210 and grounded by way of a condenser 211. Both ends of the condenser 211 are connected by way of a switch 212. Also, the output end of the operational amplifier 213 is connected to a non-inverting input end of each operational amplifier 216R, 216G and 216B, respectively, by way of switches 214R, 214G and 214B, and grounded by way of each hold condenser 215R, 215G and 215B, respectively. The output ends of the operational amplifier 216R, 216G and 216B are connected to an inverting input end of an operational amplifier 219, respectively, by way of each resistence 217R, 217G and 217E. The non-inverting input end of the operational amplifier 219 is grounded and its input end is connected to its inverting input end by way of a resistence 218. The output of the operational amplifier 219 becomes an output of the average detecting circuits 355 and 363.

Next, the operations of the average value detecting circuits 355 and 363 are illustrated as shown in FIG. 17. The switch 212 and switches 214R, 214G and 214B are turned on/off by the timing shown in FIGS. 17(c) and (d) as in the peak value detecting circuit. Then, a video signal of one color field is integrated by the resistance 200 and the condenser 201. Then, the value immediately after the reading period of each color field is sampled and held in the next sample-and-hold circuit. The ratio of the resistances 217R to 217G to 217B is established as in the peak value detecting circuit mentioned above. The gain of an adder which consists of the resistances 217R, 217G and 217B, the resistence 218 and the operational amplifier 219 is determined by $-(1/217R+1/217G+1/217B)$. 218; however, the gain of the average value detecting circuit is adjusted to be higher than the gain of the peak value detecting circuit. This is conducted in order to revise the level of average detection which is lower than the level of the peak value detection. As mentioned above, the Y signal which coincides with tho ALC and the AGC by the color frame sequential signal and its average value, is detected, and can be obtained.

The others are of the same formation, operations and effects as in the first embodiment.

Further, the present invention is not restricted by the above embodiments, for example, the A/D converter 352 which outputs the brightness establishing value can also be used by a F/V converter.

Also, each constitutive element of the automatic light control means is easily provided in either the light source apparatus 13 or the signal processing apparatus 14, and it is possible to unite the light source apparatus 13 with the signal processing apparatus 14.

Also, instead of the operating panel 334, it might be appropriate to provide a brightness establishing means and a detecting method switching means based on a switch and so on in the manipulating portion 17 of the endoscope.

Also, the present invention can be used not only in an endoscope which receives reflected light from an object to be observed but also in an endoscope which receives transmitted light from an object to be observed.

Also the automatic light control means might be suitable for controlling the quantity of light returned from an object instead of the quantity of illuminating light.

As described above, according to the present invention, it is effective that a proper photometric system can be selected in accordance with a using part and conditions of an endoscope because both of the automatic light control means and the automatic gain control means are switched to the same method of the brightness information generating means by switching the brightness information generating method with a switching means.

In this invention, it is apparent that working modes different in a wide range can be formed on the basis of this invention without deviating from the spirit and scope of the invention. This invention is not restricted by its specific working mode except being limited by the appended claims.

What is claimed is:

1. An endoscope automatic light control apparatus comprising:
   an automatic light control means for controlling the quantity of light incident to an imaging means for imaging an endoscopic image so as to maintain a signal from said imaging means substantially at a constant level;
   an automatic gain control means for inputting the signal from said imaging means and for controlling its output level so as to maintain the signal substantially at a constant level;
   said automatic light control means and said automatic gain control means respectively having a plurality of brightness information generating means for generating brightness information based on the signal from said imaging means, said plurality of brightness information generating means being different from each other in a method of generating brightness information, and one of said plurality of brightness information generating means able to be selected;

automatic light control means and said automatic gain control means respectively having a selecting means for selecting the brightness information generating means of the same method as said automatic light control means and as said automatic gain control means in said plurality of brightness information generating means;

said automatic light control means controlling the quantity of light based on said brightness information generated by said brightness information generating means selected by said selecting means; and said automatic gain control means controlling the output level based on said brightness information generated by said brightness information means selected by said selecting means.

2. An endoscope automatic light control apparatus according to claim 1, wherein said plurality of brightness information generating means includes a peak value detecting circuit for detecting a peak value of the signal from said imaging means and an average detecting circuit for detecting an average of the signal from said imaging means.

3. An endoscope automatic light control apparatus according to claim 1, wherein said automatic light control means includes an illuminating light control means for controlling the quantity of illuminating light for an endoscopic observation.

4. An endoscope automatic light control apparatus according to claim 3, wherein said illuminating light control means includes an iris disposed in the path of said illuminating light.

5. An endoscope automatic light control apparatus according to claim 1, wherein said automatic gain control means is disposed in a rear of said automatic light control means.

6. An endoscope automatic light control apparatus according to claim 1, wherein said automatic gain control means first operates after exceeding a control limit of said automatic light control means.

7. An endoscope apparatus comprising:
  an endoscope unit having a elongated insert section provided at the tip part with an observation window and an image forming optical system for receiving light reflected from an object so as to form an image of an object;
  an imaging means for imaging an image of the object formed thereon through said image forming optical system;
  a signal processing means for processing a video signal derived from said imaging means;
  an illuminating means for supplying illuminating light to a visual field of said image forming optical system;
  an automatic light control means for controlling the quantity of light incident to said imaging means so as to maintain a signal from said imaging means substantially at a constant level;
  an automatic gain control means provided in said signal processing means for inputting the signal from said imaging means and controlling its output level so as to maintain the signal substantially at a constant level;
  said automatic light control means and said automatic gain control means respectively having a plurality of brightness information generating means for generating brightness information based on the signal from said imaging means, said plurality of brightness information generating means being different from each other in a method of generating brightness information, and one of said plurality of brightness information generating means able to be selected;
  said automatic light control means and said automatic gain control means respectively having a selecting means for selecting the brightness information generating means of the same method as said automatic light control means and as said automatic gain control means in said plurality of brightness information generating means;
  said automatic light control means controlling the quantity of light based on the brightness information generated by said brightness information generating means selected by said selecting means; and
  said automatic gain control means controlling the output level based on the brightness information generated by said brightness information generating means selected by said selecting means.

8. An endoscope apparatus according to claim 7, wherein said imaging means is a solid state imaging device disposed in a focal position of said image forming optical system at the tip part of an insert section of said endoscope unit.

9. An endoscope apparatus according to claim 7, wherein said endoscope unit further comprises an eyepiece portion provided on the rear end of said insert section and image transmitting means for transmitting to said eyepiece portion the image of the object formed by said image forming optical system, and said imaging means includes a television camera detachably connected to said eyepiece portion.

10. An endoscope apparatus according to claim 7, wherein said illuminating means includes an illuminating window provided at the tip part of said insert section of said endoscope unit, a light source apparatus provided separately from said endoscope unit and illuminating light transmitting means inverted through said endoscope unit for transmitting the illuminating light from said light source apparatus to said illuminating window.

11. An endoscope apparatus according to claim 10, wherein said automatic light control means includes an illuminating light control means provided in said light source apparatus for controlling the quantity of illuminating light illuminated from said light source apparatus.

* * * * *